(12) United States Patent
Smith

(10) Patent No.: US 8,163,716 B1
(45) Date of Patent: Apr. 24, 2012

(54) METHOD OF ADMINISTERING HYALURONAN FORMULATION FOR THE AMELIORATION OF OSTEOPHYTES

(76) Inventor: James D. Smith, Lexington, KY (US)

( * ) Notice: Subject to any disclaimer, the term of this patent is extended or adjusted under 35 U.S.C. 154(b) by 413 days.

(21) Appl. No.: 12/485,265

(22) Filed: Jun. 16, 2009

Related U.S. Application Data

(60) Provisional application No. 61/076,999, filed on Jun. 30, 2008.

(51) Int. Cl.
*A61K 31/728* (2006.01)
*C07H 5/06* (2006.01)
*C08B 37/00* (2006.01)

(52) U.S. Cl. ........... 514/54; 514/62; 536/55.1; 536/55.2

(58) Field of Classification Search ................. None
See application file for complete search history.

(56) References Cited

U.S. PATENT DOCUMENTS

| | | | |
|---|---|---|---|
| 4,623,539 A | 11/1986 | Tunc | |
| 4,647,453 A | 3/1987 | Meisner | |
| 5,843,919 A | 12/1998 | Burger | |
| 5,985,850 A | 11/1999 | Falk et al. | |
| 6,013,641 A | 1/2000 | Lussow et al. | |
| 6,162,787 A | 12/2000 | Sorgente et al. | |
| 6,255,295 B1 | 7/2001 | Henderson et al. | |
| 6,333,304 B1 | 12/2001 | Bath et al. | |
| 6,346,519 B1 | 2/2002 | Petrus | |
| 6,387,382 B1 | 5/2002 | Saleh et al. | |
| 6,391,861 B1 | 5/2002 | Cantor | |
| 6,391,864 B1 | 5/2002 | Stone | |
| 6,432,929 B1 | 8/2002 | Stone | |
| 6,451,771 B1 | 9/2002 | Henderson et al. | |
| 6,476,005 B1 * | 11/2002 | Petito et al. | 514/62 |
| 6,537,978 B1 | 3/2003 | Turley | |
| 6,607,745 B2 * | 8/2003 | Leneau | 424/439 |
| 6,608,041 B2 | 8/2003 | Hammerly | |
| 6,620,927 B2 | 9/2003 | Bulpitt et al. | |
| 6,645,945 B1 * | 11/2003 | Radomsky et al. | 514/54 |
| 6,706,267 B1 | 3/2004 | Adalsteinsson et al. | |
| 6,924,273 B2 | 8/2005 | Pierce | |
| 6,979,679 B2 | 12/2005 | Marcum | |
| 7,811,612 B2 | 10/2010 | Kim et al. | |
| 2002/0173484 A1 * | 11/2002 | Leneau | 514/54 |
| 2004/0198695 A1 * | 10/2004 | Li et al. | 514/54 |

OTHER PUBLICATIONS

"Bone Spurs", downloaded from MayoClinic.com, revised Jan. 5, 2010, pp. 1-6.*
Kim et al., "Therapeutic Effect of Hyaluronic Acid on Experimental Osteoarthritis of Ovine Temporomandibular Joint" J. Vet. Med. Sci. (2001) vol. 63 No. 10, pp. 1083-1089.*
Merriam-Webster's Collegiate Dictionary, Tenth Edition, published 1998 by Merriam-Webster, Incorporated, p. 924.*
U.S. Appl. No. 12/572,641, filed Oct. 2009, Smith, James D.*
Jebens et al., "On the Viscosity and pH of Synovial Fluid and the pH of Blood" The Journal of Bone and Joint Surgery (1959) vol. 41 B No. 2 pp. 388-400.*
United States Patent and Trademark Office; Office Action; mailed Oct. 26, 2010; in U.S. Appl. No. 12/572,641.
Response to Office Action in U.S. Appl. No. 12/572,641, electronically filed on Jan. 24, 2011.
James D. Smith, "Method of Administering Hyaluronan Formulation for the Amelioration of Osteoarthritis", U.S. Appl. No. 12/165,278, filed Jun. 30, 2008. (Pending).
James D. Smith, "Method of Administering Hyaluronan Formulation for the Amelioration of Osteoarthritis", U.S. Appl. No. 12/572,641, filed Oct. 2. 2009. (Pending).
James D. Smith, "Method of Administering Hyaluronan Formulation for the Amelioration of Osteopenia", U.S. Appl. No. 12/485,596, filed Jun. 16, 2009, (Pending).
James D Smith. "Hyaluronan Formulation". U.S. Appl. No. 11/595,657, filed Nov. 11, 2006, (Abandoned).
Office Action mailed Sep. 14, 2008 in U.S. Appl. No. 11/595,657.
Response to Office Action mailed Sep. 14, 2008 and electronically submitted on Mar. 13, 2009.
Office Action mailed Jul. 23, 2009 in U.S. Appl. No. 11/595,657.
Mary K. Cowman, "$^1$H NMR of Glycosaminoglycans and Hyaluronic Acid Oligosaccharirdes in Aqueous Solution: The Amide Proton Environment", Archives of Biochemistry and Biophysics, vol. 230, No. 1, pp. 203-212, Apr. 1984.
Mary K. Cowman, "$^1$H NMR of Glycosaminoglycans and Hyaluronic Acid Oligosaccharirdes in Aqueous Solution: The Amide Proton Environment", Archives of Biochemistry and Biophysics, vol. 230, No. 1, pp. 203-312, Apr. 1984, (Abstract only).
M.F. McCarty, et al., "Sulfated Glycosaminoglycans and Glucosamine May Synergize in Promoting Synovial Hyaluronic Acid Synthesis". Medical Hypothesis (2000) 54(5), 798-802, Mar. 17, 1999.
M. Anthony Pogrel, et al., "Hyaluronan (hyaluronic acid) in Human Saliva". Archives of Oral Biology, vol. 41, No. 7, pp. 667-671. (1996).
A. Rossler. et al.. "Plasma Hyaluronan Concentration: No Circadian Rhythm but Large Effect of Food Intake in Humans", Eur J Appl Physiol, vol. 78, No. 6, pp. 573-577, (1998).
Hideki Sato, et al., Antioxidant Activity of Synovial Fluid, Hyaluronic Acid, and Two Subcomponents of Hyaluronic Acid, Arthritis and Rheumatism, vol. 31, No. 1 (Jan. 1998).
Chris Tuckwell, "Velvet Antler, a Summary of the Literature on Health Benefits", Australian Government Rural Industries Research and Development Corporation, Nov. 2003.

(Continued)

*Primary Examiner* — Eric S Olson
(74) *Attorney, Agent, or Firm* — Curatolo Sidoto Co., LPA; Joseph G. Curatolo; Salvatore A. Sidoti

(57) ABSTRACT

Disclosed is a method for the amelioration of osteophyte formation including administering to a subject a therapeutically effective amount of an exogenous hyaluronan formulation.

43 Claims, 1 Drawing Sheet

OTHER PUBLICATIONS

M. Anthony Pogrel, et al., "Hyaluronan (hyaluronic acid) and Its Regulation in Human Saliva by Hyaluronidase and its Inhibitors", Journal of Oral Science, vol. 45, No. 2, 2003, pp. 85-91, Publication Date: May 19, 2003.

* cited by examiner

METHOD OF ADMINISTERING HYALURONAN FORMULATION FOR THE AMELIORATION OF OSTEOPHYTES

CROSS REFERENCE TO RELATED APPLICATIONS

This application claims the benefit of the filing date under 35 U.S.C. §119(e) of U.S. Provisional Application For Patent Ser. No. 61/076,999 filed on Jun. 30, 2008, which is hereby incorporated by reference.

TECHNICAL FIELD

The present disclosure relates to a method of administering a composition comprising a therapeutically effective amount of an exogenous hyaluronan to a vertebrate subject for preventing, slowing, attenuating, mitigating, and/or ameliorating the formation of osteophytes in bone remodeling in the Subject.

BACKGROUND

Osteophytes, commonly called bone spurs, are bony projections that develop along the edges of bones. They may form on any bone including vertebrae, and often form where bones meet at joints. Osteophytes may also develop where ligaments and tendons connect to bone. Range of motion is frequently limited in the affected joint and although osteophytes themselves are not painful, they frequently rub against nerves and cause pain. All vertebrate species are subject to the development of osteophytes.

Osteophyte formation has been classically related to any sequential and consequential changes in bone formation due to aging, degeneration, mechanical instability, and disease. For forty-two percent of the adult human population, degeneration and development of osteophytes will lead to symptoms of neck and back pain, radiating arm and leg pain, and weakness in the extremities during their lifetime.

Medical treatments for osteophytes are typically palliative and not directed at the underlying problem. Osteophytes that limit range of motion or cause other problems that limit ability may require surgery to prevent further joint damage. Surgical options are determined by the location of the osteophyte. Osteophytes are often removed as part of a more comprehensive surgery for osteoarthritis. For example, with osteoarthritis in an elbow the surgeon may remove osteophytes while making other repairs to the joint. Access to the joint for removal of osteophytes may be via arthroscopic surgery or with an open procedure.

There is no teaching in the art of a method for preventing, slowing, attenuating, mitigating, and/or ameliorating the formation of osteophytes in bone remodeling in a vertebrate subject by administering a composition comprising a therapeutically effective amount of an exogenous hyaluronan to the subject. The present disclosure provides such a method.

SUMMARY

Disclosed is a method for preventing, slowing, attenuating, mitigating, and/or ameliorating the formation of osteophytes in hone remodeling in a vertebrate subject, the method comprising administering a composition comprising a therapeutically effective amount of an exogenous hyaluronan formulation to the vertebrate subject.

DETAILED DESCRIPTION

Figure 1:
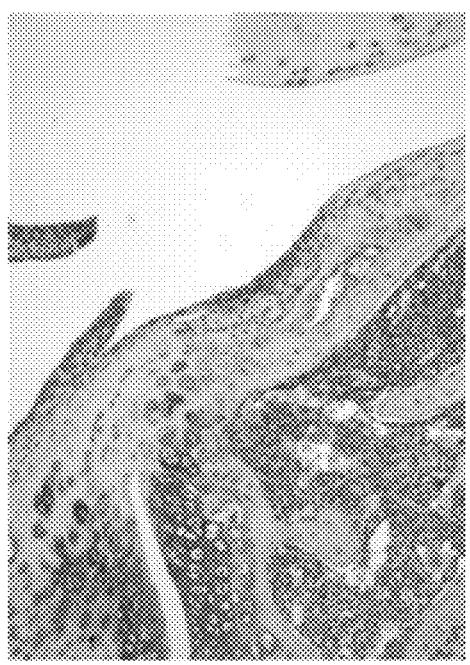
FIG. 1 is a photograph of the histopathology tissue section of Control Mouse 1.

Disclosed is a method of administering a modified hyaluronan biopolymer to a vertebrate subject for the purposes of preventing, slowing, attenuating, mitigating, and/or ameliorating the formation of osteophytes. The method comprises administering a composition comprising a therapeutically effective amount of exogenous hyaluronan biopolymer to the subject.

The method of administering a therapeutically effective amount of the hyaluronan biopolymer to a subject may be accomplished by any means known in the art, such as, without limitation, oral or parenteral administration. According to certain illustrative embodiments, parenteral administration of the therapeutically effective amount of the hyaluronan may comprise subcutaneous administration, intramuscular administration, and intravenous administration.

A therapeutically effective amount of hyaluronan biopolymer per kg body weight of the test subject can be determined by one having ordinary skill in the art without having to resort to undue experimentation. According to certain illustrative embodiments, and without limitation, therapeutically effective amounts may comprise from about 0.2 to about 5 mg per kg body weight of the subject per day, from about 0.4 to about 4 mg per kg body weight of the subject per day, from about 0.6 to about 3 mg per kg body weight of the subject per day, from about 0.8 to about 2 mg per kg body weight of the subject per day, and about 1 mg per kg body weight of the subject per day. The daily therapeutically effective amount of the hyaluronan biopolymer may be administered to the subject as a single dose comprising the entire therapeutically effective amount. Alternatively, the therapeutically effective amount of the hyaluronan biopolymer may be achieved by administering in multiple lower amounts that cumulatively achieve the daily therapeutically effective amount.

The term "hyaluronan" as used herein refers to hyaluronic acid or any physiological salt form of hyaluronic acid. The hyaluronan biopolymer may be polydisperse and therefore comprises a mixture of polymers having different molecular masses. In certain embodiments, the hyaluronan biopolymer is polydisperse and therefore comprises a mixture of polymers having different molecular masses. Without limitation, the hyaluronan biopolymer that is administered to the vertebrate subject may comprise molecular weights in range from about 50,000 to about 8,000,000 Daltons. By way of illustration, suitable hyaluronan may comprise molecular weights from about 500,000 to about 2,500,000 Daltons, from about 750,000 to about 2,250,000 Daltons, from about 1,000,000 to about 2,000,000 Daltons, from about 1,250,000 to about 1,750,000 Daltons, or from about 1,375,000 to about 1,625,000 Daltons. According to certain embodiments, the biopolymer comprises a weight average molecular weight of about 1,500.000 Daltons.

Without limitation, the physiological salt form may comprises an alkali metal salt. For example, according to an illustrative embodiment, the physiological salt may comprise sodium hyaluronate.

According to illustrative embodiments, the biopolymer composition comprises a product of microbial fermentation. By producing the polymer by extra-cellular microbial fermentation, it is considered to be a vegan product. Accordingly, the hyaluronan may contain no animal derived materials, which minimizes the risk of transmission of animal spongiform encephalopathy. Producing the hyaluronan polymer by microbial fermentation also results in more consistent molecular profile, molecular weight and narrow polydispersity that is optimized for oral bioavailibility.

The hyaluronan composition comprises a pharmaceutically acceptable carrier that is safe for human or veterinary consumption. Without limitation, and by way of example only, a suitable carrier for the hyaluronan composition is water.

The hyaluronan composition further comprises at least one pharmaceutically acceptable excipient. Without limitation, and by way of example only, a suitable excipient for the hyaluronan composition comprises sodium chloride.

The hyaluronan composition may also include a pH altering agent. Without limitation, and by way of example only, a suitable pH altering agent for the hyaluronan composition comprises citric acid. According to certain embodiments, and without limitation, citric acid is included in the hyaluronan composition in an amount effective to provide a pH of the hyaluronan composition that is between about 2.5 and about 4.5.

According to certain illustrative embodiments, the composition comprises a therapeutically effective amount of hyaluronan and an antimicrobial preservative. Any known antimicrobial preservative that is generally regarded as safe for human or veterinary consumption may be included in the hyaluronan composition. Without limitation, suitable antimicrobial preservatives include potassium sorbate, sodium benzoate and mixtures thereof The biopolymer composition and method of administration may be useful for prevention of the formation of osteophytes in a wide variety of vertebrate species. For example, and by way of example only, the hyaluronan composition may be administered to any of human, equine, canine or feline species.

The hyaluronan may be formulated into a wide variety of orally ingestible compositions. The hyaluronan may be formulated with an acceptable carrier to provide an orally ingestible liquid or a solid or semi-solid food product. Liquid forms include solutions, suspensions, emulsions, syrups and the like. According to certain illustrative embodiments, the hyaluronan composition may be formulated with an orally ingestible liquid carrier to provide an orally ingestible hyaluronan composition. For example, the hyaluronan may be formulated with an orally ingestible liquid carrier to provide a beverage, dietary supplement formulation, or nutritional supplement. The beverages, dietary supplements and nutritional supplements may be provided ready for oral ingestion or may be provided in a concentrate that requires dilution with acceptable liquids prior to oral ingestion. According to alternative embodiments, the hyaluronan may be formulated into other orally ingestible product forms, such as powders, pills, lozenges, tablets, caplets, capsules, gel capsules and the like. Flavoring agents may also be added to the hyaluronan compositions to provide a more palatable orally ingestible composition.

The orally administrable hyaluronan composition may further include nutritionally effective amounts of an additional supplement. According to certain embodiments, the hyaluronan composition further comprises nutritionally effective amounts of at least one vitamin, or at least one mineral or a combination of at least one vitamin and at least one mineral. According to certain embodiments, the hyaluronan composition comprises a therapeutically effective amount of hyaluronan and a nutritionally effective amount of at least one vitamin. According to certain embodiments, the hyaluronan composition comprises a therapeutically effective amount of hyaluronan and a nutritionally effective amount of more than one different vitamin. According to certain embodiments, the hyaluronan composition comprises a therapeutically effective amount of hyaluronan and a nutritionally effective amount of at least one mineral. According to certain embodiments, the hyaluronan composition comprises a therapeutically effective amount of hyaluronan and a nutritionally effective amount of more than one different mineral. According to certain embodiments, the hyaluronan composition comprises a therapeutically effective amount of hyaluronan and a nutritionally effective amount of at least one vitamin and at least one mineral. According to certain embodiments, the hyaluronan composition comprises a therapeutically effective amount of hyaluronan and a nutritionally effective amount of more than one different vitamin and at least one mineral. According to certain embodiments, the hyaluronan composition comprises a therapeutically effective amount of hyaluronan and a nutritionally effective amount of at least one vitamin and more than one different mineral. According to certain embodiments, the hyaluronan composition comprises a therapeutically effective amount of hyaluronan and a nutritionally effective amount of more than one different vitamin and more than one different mineral.

The hyaluronan composition may also include a drug component alone or in addition to the nutritional supplemental.

EXAMPLES

The following examples are provided to further illustrate the hyaluronan composition and method of administering the exogenous hyaluronan to vertebrate subjects. It should be noted that the examples are provided for illustration and should not be construed to limit the scope of the composition or method of administering the composition in any manner.

Bone Remodeling/Osteophyte Formation

A study was designed and conducted to examine the effect of an orally administered exogenous hyaluronan biopolymer to prevent poor bone remodeling and osteophyte development. A total of 10 inbred laboratory mice were obtained and housed according to accepted laboratory animal standards. The mice underwent an aggressive knee instability surgery. The medial collateral and anterior cruciate ligaments were identified and transected followed by a partial meniscectomy.

Following surgery mice were randomly assigned to two groups. Control Group (N=5) were gavaged 5 days/week for 4 weeks with saline. Treatment Group (N=5) was savaged 5 days/week with MHB3™ hyaluronan formulation (Cogent Solutions Group LLC, Lexington, Ky.) at a dose of 10 mg/kg, for five weeks. During the five weeks post-surgery, it was anticipated that all animals would have severe bone remodeling and osteophyte development. After five weeks of treatment the mice were euthanized, their knees decalcified, paraffin embedded, stained with Saffrin-O and evaluated on slides.

Figure 2:
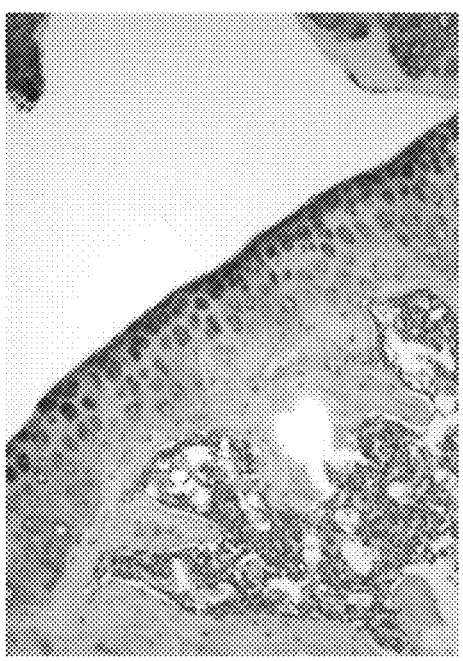
FIG. 2 is a photograph of the histopathology tissue section of Treatment Mouse 2.

As shown in the tissue sample of FIG. 1 (Control Mouse), the red-staining tissue with poorly defined margins on the interior of the bone tissue is indicative of a failed attempt to remodel the bone and the formation of osteophytes leading to severe instability. On the other hand, the tissue sample of FIG. 2 (Treatment Mouse) which was orally administered the hyaluronan composition exhibits well-defined bright red-staining tissue on the surface of the bone. The well-defined margins of red-staining tissue are indicative of intake and healthy bone surfaces without the formation of osteophytes. These results demonstrate the effectiveness of the oral administration of therapeutically effective amounts of an exogenous hyaluronan biopolymer to mice having undergone knee instability surgery, as compared to those mice receiving a control composition comprising normal saline.

This is the first time, to our knowledge, that an orally administered, exogenous hyaluronan biopolymer has been shown to have bone protecting benefits including but not limited osteophyte prevention.

Likewise, through parenteral administration of a buffered hyaluronan solution, such as through subcutaneous or intramuscular administration, similar effects are observed. It will be apparent to those skilled in the art to which the present invention pertains how to make and how to use such a buffered hyaluronan solution for parenteral administration.

While the method for administering hyaluronan to vertebrate subject has been described above in connection with certain illustrative embodiments, it is to be understood that other embodiments may be used or modifications and additions may be made to the described embodiments for performing the same function without deviating therefrom. Furthermore, all embodiments disclosed are not necessarily in the alternative, as various embodiments may be combined to provide the desired characteristics. Variations can be made by one having ordinary skill in the art without departing from the spirit and scope of the disclosed method. Therefore, the method should not be limited to any single embodiment, but rather construed in breadth and scope in accordance with the recitation of the attached claims. Equivalents will be readily apparent to those skilled in the art.

I claim:

1. A method for slowing, attenuating, mitigating, and/or ameliorating the formation of osteophytes in a vertebrate subject, the method comprising administering a composition consisting essentially of a therapeutically effective amount of hyaluronan to the subject, wherein the pH of the composition is between about 2.5 and about 4.5.

2. The method of claim 1, wherein the administering comprises oral administration.

3. The method of claim 1, wherein the administering comprises parenteral administration.

4. The method of claim 3, wherein the parenteral administration comprises subcutaneous administration.

5. The method of claim 3, wherein the parenteral administration comprises intramuscular administration.

6. The method of claim 3, wherein the parenteral administration comprises intravenous administration.

7. The method of claim 1, wherein the composition comprises from about 0.2 to about 5 mg hyaluronan per kg body weight of the subject per day.

8. The method of claim 7, wherein the composition comprises from about 0.4 to about 4 mg hyaluronan per kg body weight of the subject per day.

9. The method of claim 8, wherein the composition comprises from about 0.6 to about 3 mg hyaluronan per kg body weight of the subject per day.

10. The method of claim 9, wherein the composition comprises from about 0.8 to about 2 mg hyaluronan per kg body weight of the subject per day.

11. The method of claim 10, wherein the composition comprises about 1 mg hyaluronan per kg body weight of the subject per day.

12. The method of claim 1, wherein the composition further comprises at least one pharmaceutically acceptable excipient.

13. The method of claim 12, wherein the composition comprises water.

14. The method of claim 13, wherein the composition comprises sodium chloride.

15. The method of claim 13, wherein the composition comprises citric acid.

16. The method of claim 12, wherein the composition comprises an antimicrobial preservative.

17. The method of claim 16, wherein the preservative is at least one of potassium sorbate and sodium benzoate.

18. The method of claim 1, wherein the hyaluronan is polydisperse comprising molecular weights from about 500,000 to about 2,500,000 Daltons.

19. The method of claim 18, wherein the hyaluronan is polydisperse comprising molecular weights from about 750,000 to about 2,250,000 Daltons.

20. The method of claim 19, wherein the hyaluronan is polydisperse comprising molecular weights from about 1,000,000 to about 2,000,000 Daltons.

21. The method of claim 20, wherein the hyaluronan is polydisperse comprising molecular weights from about 1,250,000 to about 1,750,000 Daltons.

22. The method of claim 21, wherein the hyaluronan is polydisperse comprising molecular weights from about 1,375,000 to about 1,625,000 Daltons.

23. The method of claim 22, wherein the hyaluronan is of median molecular weight about 1,500,000 Daltons.

24. The method of claim 1, wherein the hyaluronan is a product of microbial fermentation.

25. The method of claim 1, wherein the subject is a human subject.

26. The method of claim 1, wherein the subject is an equine subject.

27. The method of claim 1, wherein the subject is a canine subject.

28. The method of claim 1, wherein the subject is a feline subject.

29. The method of claim 1, wherein the formation of osteophytes is a result of injury.

30. The method of claim 1, wherein the formation of osteophytes is a result of a process other than injury.

31. The method of claim 1, wherein the method comprises disease modification.

32. A method for slowing, attenuating, mitigating, and/or ameliorating the formation of osteophytes in a vertebrate subject, the method comprising administering by of one subcutaneous administration, intramuscular administration, intravenous administration, or a combination thereof a composition comprising a therapeutically effective amount of hyaluronan to the subject, wherein the pH of the composition is between about 2.5 and about 4.5.

33. The method of claim 32, wherein the composition comprises from about 0.2 to about 5 mg hyaluronan per kg body weight of the subject per day.

34. The method of claim 33, wherein the composition comprises from about 0.4 to about 4 mg hyaluronan per kg body weight of the subject per day.

35. The method of claim 34, wherein the composition comprises from about 0.6 to about 3 mg hyaluronan per kg body weight of the subject per day.

36. The method of claim 35, wherein the composition comprises from about 0.8 to about 2 mg hyaluronan per kg body weight of the subject per day.

37. The method of claim 36, wherein the composition comprises about 1 mg hyaluronan per kg body weight of the subject per day.

38. The method of claim 32, wherein the hyaluronan is polydisperse comprising molecular weights from about 500,000 to about 2,500,000 Daltons.

39. The method of claim 38, wherein the hyaluronan is polydisperse comprising molecular weights from about 750,000 to about 2,250,000 Daltons.

40. The method of claim 39, wherein the hyaluronan is polydisperse comprising molecular weights from about 1,000,000 to about 2,000,000 Daltons.

41. The method of claim 40, wherein the hyaluronan is polydisperse comprising molecular weights from about 1,250,000 to about 1,750,000 Daltons.

42. The method of claim 41, wherein the hyaluronan is polydisperse comprising molecular weights from about 1,375,000 to about 1,625,000 Daltons.

43. The method of claim 42, wherein the hyaluronan is of median molecular weight about 1,500,000 Daltons.

* * * * *